United States Patent [19]

Victor et al.

[11] Patent Number: 5,363,199
[45] Date of Patent: Nov. 8, 1994

[54] SMOKE OPACITY DETECTOR

[76] Inventors: Bruce H. Victor, 34 Cutlass Rd., Kinnelon, N.J. 07405; Michael M. Katz, 13 Summit Ave., New City, N.Y. 10956

[21] Appl. No.: 182,741

[22] Filed: Jan. 14, 1994

[51] Int. Cl.⁵ .......................................... G01N 21/61
[52] U.S. Cl. ................................... 356/439; 250/573; 422/78
[58] Field of Search ...................... 356/437, 438, 439; 422/78, 80; 250/573, 339.03

[56] References Cited

U.S. PATENT DOCUMENTS

| | | |
|---|---|---|
| 3,544,218 | 12/1970 | Cassidy . |
| 3,811,839 | 5/1974 | Di Pietro et al. ................. 356/439 |
| 3,926,562 | 12/1975 | Williams et al. .................. 422/78 |
| 3,973,852 | 8/1976 | Moore et al. . |
| 5,092,674 | 3/1992 | Garner . |
| 5,110,214 | 5/1992 | Battiste et al. . |
| 5,148,234 | 9/1992 | Tamm et al. . |
| 5,163,332 | 11/1992 | Wong . |
| 5,220,179 | 6/1993 | Gagea . |

Primary Examiner—Richard A. Rosenberger
Attorney, Agent, or Firm—Richard M. Goldberg

[57] ABSTRACT

A smoke opacity detector includes a sample chamber; a sample heating block in the sample chamber for heating a sample; a first temperature control for controlling the temperature of the sample heating block to a desired temperature; a measurement stack positioned above the sample heating block for receiving smoke resulting from heating of the sample by the sample heating block; a laser light source for projecting a light beam through the smoke in the measurement stack; a photodetector for detecting the amount of light from the laser light source that passes through the smoke in the measurement stack; a microprocessor for determining the amount of smoke resulting from heating of the sample, in response to the light detected by the photodetector; and a device for selectively eliminating conditions of water vapor in the determination of the amount of smoke by the microprocessor, the device for selectively eliminating including a heating device for heating the measurement stack and a second temperature control for selectively controlling the temperature of the measurement stack to a selected temperature above 100° C. to render the water vapor gaseous and thereby eliminate affects of water vapor on the determination, and a temperature below 100° C. to include affects of water vapor on the determination.

26 Claims, 1 Drawing Sheet

SMOKE OPACITY DETECTOR

BACKGROUND OF THE INVENTION

The present invention relates generally to apparatus for detecting emission levels of air pollutants, and more particularly, is directed to a smoke opacity detector.

The Federal Clean Air Act requires all companies having exhaust stacks to restrict the amount of visual emissions therefrom to a specific range. The Environmental Protection Agency (EPA) sets the standards for complying with this Act. If a company fails to comply with this requirement, it may be subject to sanctions including fines, mandated installation of air pollution control equipment, and legal actions to prevent the company from operating. In addition, various state environmental laws of a similar nature are enforced by state environmental agencies.

As an example, in the specific application of a textile finishing operation, solvents or chemicals are used which are subjected to very high temperature conditions. As a result thereof, smoke (gas containing particulate impurities) is produced and emitted into the atmosphere.

Various devices are known which test the amount of smoke from a material.

For example, in U.S. Pat. No. 3,544,218 to Cassidy, a specimen which is held by a specimen holder in a burning chamber is burnt by an ignition flame from a gas burner nozzle. The amount of the flame and heat required for different materials being tested can be varied. Smoke collected in the chamber is exhausted through an exhaust duct into a smoke detecting device having a light unit and a photoelectric cell. However, because a gas burner nozzle is used, it is difficult to control the heat to an exact temperature. Further, the smoke must travel out of the chamber into a separate conduit, which may affect the final measurement due to dispersement of the gas. It is further noted that the EPA has determined that water vapor is not a contaminant. Accordingly, in many situations, the effects of water vapor on the smoke detector should be eliminated. However, with Cassidy, there are no means for taking into account conditions for water vapor.

U.S. Pat. No. 3,973,852 to Moore et al discloses a method and apparatus for measuring particulate concentration in the atmosphere. However, Moore et al does not burn a sample and measure smoke opacity, but rather, only measures atmospheric pollution at a particular location using a laser light beam and a receiver. Moore et al does discuss the need to eliminate conditions of water vapor. This is accomplished, however, by a complex arrangement using monochromatic laser pulses.

U.S. Pat. No. 5,110,214 to Battiste et al discloses an apparatus for evaluating the propensity of polymers for smoking during processing, that is, for measuring the smoke emitted when the polymer is melted and extruded. The temperature for burning the gases is controlled by heater bands, although it is stated that an automated melt indexer or other rheometer may be used to melt and extrude the polymer. The gases that are burned from the sample are supplied through a side arm opening and tube to an aerosol monitor for analysis of smoke content. The smoke content in the monitor is determined by any of a plurality of different disclosed light detecting means. The output from the smoke detector is compared with known values for known compositions and/or different particle sizes. However, there is no control provided to take into account the effects of water vapor.

U.S. Pat. No. 5,220,179 to Gagea discloses an apparatus for detecting the presence of vapor and/or smoke in the outgoing air of a device for heating materials. Specifically, the smoke from a sample in a microwave unit travels to an exhaust pipe. Light from a light source is either transmitted (unobstructed) to a light receiver, absorbed by the smoke particles or reflected by the vapor particles to the light receiver. In this manner, water vapor conditions can be controlled. Therefore, the detection of water vapor in the smoke is determined by the reflected light. However, besides being a complex arrangement to account for water vapor, Gagea does not eliminate water vapor from the smoke to be detected, but rather, must provide a separate determination.

U.S. Pat. No. 5,163,332 to Wong discloses a gas sample chamber connected at one end to a source chamber which contains a small incandescent lamp or other light source and at the other end is connected to a detector. Wong shows heater wires attached to the outside of the tube of the gas sample chamber and which prevent condensation of water vapor on the inside of the tube. However, Wong uses specular reflection along the walls of the chamber, and is therefore only concerned with water vapor condensing on the walls in small droplets, rather than water vapor being present in the gas itself. Also, Wong is not concerned with smoke detection, but rather, only with gas analysis, and for this reason, Wong specifically keeps dust and smoke particles out of the sample chamber by a sheet of semipermeable membrane that functions as a filter.

Other patents of interest are U.S. Pat. No. 5,092,674 to Garner and U.S. Pat. No. 5,148,234 to Tamm et al.

OBJECTS AND SUMMARY OF THE INVENTION

Accordingly, it is an object of the present invention to provide a smoke opacity detector that overcomes the problems with the aforementioned prior art.

It is another object of the present invention to provide a smoke opacity detector that detects the amount of contaminants in the emitted smoke of a chemical prior to using the same in an industrial operation.

It is still another object of the present invention to provide a smoke opacity detector that permits the testing of different chemicals to determine which one will satisfy environmental standards.

It is yet another object of the present invention to provide a smoke opacity detector that can selectively eliminate the effects of water vapor on the measured results.

It is a further object of the present invention to provide a smoke opacity detector in which the water vapor can be made totally gaseous so as not to affect any measurements.

It is a still further object of the present invention to provide a smoke opacity detector which enables a company to reduce visual emissions from a facility while minimizing the use of expensive air pollution control techniques.

It is a yet further object of the present invention to provide a smoke opacity detector which enables a company to identify chemicals causing emissions problems so as to avoid problems with federal, state, and local environmental enforcement agencies.

In accordance with an aspect of the present invention, a smoke opacity detector includes a sample chamber; a sample heating block in the sample chamber for heating a sample; a first temperature control for controlling the temperature of the sample heating block to a desired temperature; a measurement stack positioned above the sample heating block for receiving smoke resulting from heating of the sample by the sample heating block; a light source for projecting a light beam through the smoke in the measurement stack; a photodetector for detecting the amount of light from the light source that passes through the smoke in the measurement stack; a determining circuit for determining the amount of smoke resulting from heating of the sample, in response to the light detected by the photodetector; and a device for selectively eliminating conditions of water vapor in the determination of the amount of smoke by the determining circuit, the device for selectively eliminating including a heating device for heating the measurement stack and a second temperature control for selectively controlling the temperature of the measurement stack to a selected temperature above 100° C. to render the water vapor gaseous and thereby eliminate affects of water vapor on the determination, and a temperature below 100° C. to include affects of water vapor on the determination.

Preferably, the sample heating block includes heating wires therein for heating the sample heating block to a temperature in the range of approximately 50° C. to 600° C.

The measurement stack is of a generally tubular nature and is positioned directly above the sample heating block. The measurement stack extends along a longitudinal axis thereof and includes first and second diametrically opposite windows therein which extend along a line transverse to the longitudinal axis.

The light source is positioned adjacent the first window so as to project the light beam through the first window toward the second window, and the photodetector is positioned adjacent the second window for detecting the amount of light from the light source that passes through the first window, the smoke in the measurement stack and the second window. Preferably, the light source includes a red helium neon laser light source.

The determining circuit includes a circuit for determining a difference between a determined value corresponding to the amount of smoke resulting from heating of the sample and a standard value, and for integrating the difference to produce an output which is a determination of whether the determined value is greater or less than the standard value. Preferably, the determining circuit includes a microprocessor.

To control water vapor conditions, heating wires are provided in the measurement stack for heating the measurement stack to selectively render the water vapor gaseous to thereby eliminate affects of water vapor on the determination.

In addition, a sample injection port extends through the chamber for supplying a predetermined amount of the sample through the measurement stack onto the sample heating block.

In addition, the measurement stack preferably includes third and fourth diametrically opposite windows therein which extend along a line transverse to the longitudinal axis, and which are positioned at heights above the first and second windows. An infrared light is positioned adjacent the third window so as to project an infrared light beam through the third window toward the fourth window, and an infrared photodetector is positioned adjacent the fourth window for detecting the amount of infrared light from the infrared light that passes through the third window, the smoke in the measurement stack and the fourth window, and for supplying an output signal to the microprocessor for infrared spectrophotometry.

In accordance with another aspect of the present invention, a method of detecting smoke opacity includes the steps of heating a sample on a sample heating block in a chamber to produce smoke; controlling the temperature of the sample heating block to a desired temperature; projecting a light beam from a light source through the smoke passing through a measurement stack positioned above the sample heating block; detecting the amount of light from the light source that passes through the smoke in the measurement stack; determining the amount of smoke resulting from heating of the sample, in response to the amount of detected light; and selectively eliminating conditions of water vapor in the determination of the amount of smoke, the step of selectively eliminating including the steps of heating the measurement stack and selectively controlling the temperature of the measurement stack to a selected temperature above 100° C. to render the water vapor gaseous and thereby eliminate affects of water vapor on the determination, and a temperature below 100° C. to include affects of water vapor on the determination.

The above and other objects, features and advantages of the invention will become readily apparent from the following detailed description thereof which is to be read in connection with the accompanying drawing.

DETAILED DESCRIPTION OF THE PREFERRED EMBODIMENTS

Figure 1:
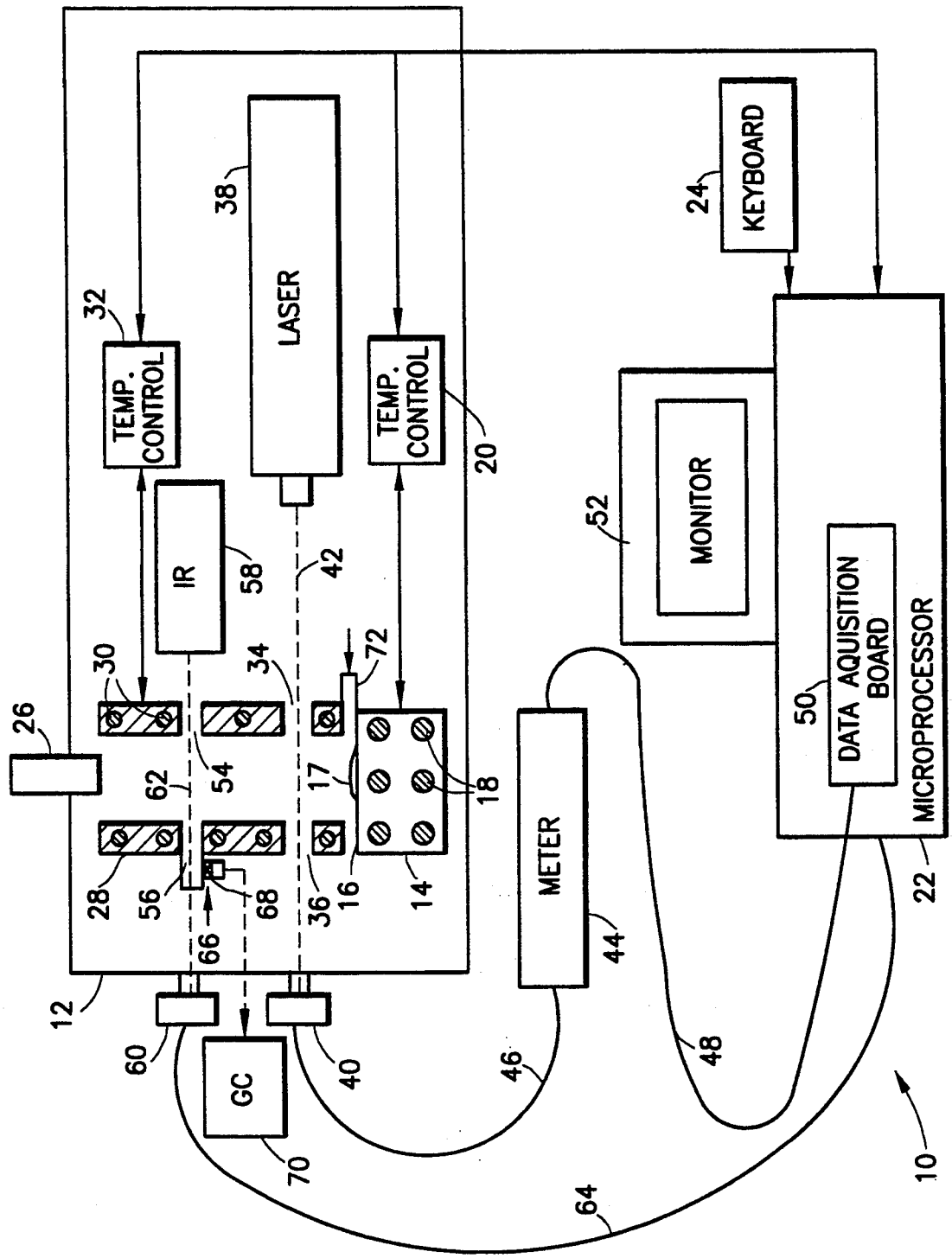
FIG. 1 is schematic block diagram of a smoke opacity detector according to the present invention.

Referring to FIG. 1 in detail, a smoke opacity detector 10 according to the present invention includes a cabinet 12 containing a sample heating block 14 with an upper surface 16 for holding a sample 17 to be tested. Sample heating block 14 is preferably of a heat conducting metal material, and a plurality of heating elements, such as heating wires 18, are embedded within heating block 14 for heating the same. It will be appreciated that other means may be provided for heating sample heating block 14, such as heat exchanger tubes passing therethrough, heating blanket means thereover, or the like.

A temperature controller 20 is provided in association with heating block 14, and a microprocessor 22 is used in conjunction with temperature controller 20 to adjust the temperature of heating block 14 to a desired temperature. For example, temperature controller 20 may include a conventional thermistor or other temperature sensing element (not shown) for sensing the temperature of heating block 14 and for supplying the sensed temperature to microprocessor 22. In addition, temperature controller 20 may include a conventional current regulation circuit (not shown) which controls the amount of current and/or times during which current is supplied to heating wires 18. Preferably, microprocessor 22 utilizes conventional proportional, integral, and reset control theory to control temperature controller 20 to hold the temperature of block 14 constant. Alternatively, and preferably, instead of using a separate microprocessor 22, a microprocessor may be built into temperature controller 20, and such a temperature controller is a conventional item sold, for example, by Omega Corp. of Stamford, Conn.

The temperature of sample heating block 14 can be set to a desired temperature by the user through a keyboard 24 connected with microprocessor 22. Typically, this temperature is the highest temperature that the chemical sample 17 will be subjected to during an actual industrial operation, to obtain the same smoke evolution. Preferably, the heating range of heating block 14 will be in the range of approximately 50° C. to 600° C.

A sample injection port 26 is provided through cabinet 12 and positioned above heating block 14. Accordingly, a sample 17 of the chemical to be used is supplied to sample injection port 26 and falls onto upper surface 16 of sample heating block 14. The amount of sample 17 that is used can vary, although typical sample sizes are between ½ and 1 milliliter.

As a result thereof, a portion of sample 17 is volatilized, so that smoke containing particulate contaminants (condensed particles) is produced, and rises upwardly.

Smoke opacity detector 10 further includes a measurement stack 28 of a generally tubular configuration which is positioned directly above upper surface 16 of sample heating block 14, and through which the sample 17 to be tested falls from sample injection port 26 to upper surface 16. Measurement stack 28 preferably has its longitudinal axis extending vertically. A plurality of heating elements, such as heating wires 30, are embedded within measurement stack 28 for heating the same. It will be appreciated that other means may be provided for heating measurement stack 28, such as heat exchanger tubes passing therethrough, heating blanket means thereover, or the like.

A temperature controller 32 is provided in association with measurement stack 28, and microprocessor 22 is used in conjunction with temperature controller 32 to adjust the temperature of measurement stack 28 to a desired temperature. For example, temperature controller 32 may include a conventional thermistor or other temperature sensing element (not shown) for sensing the temperature of measurement stack 28 and for supplying the sensed temperature to microprocessor 22. In addition, temperature controller 32 may include a conventional current regulation circuit (not shown) which controls the amount of current and/or times during which current is supplied to heating wires 30. As shown, microprocessor 22 again utilizes conventional proportional, integral, and reset control theory to control temperature controller 32 to hold the temperature of measurement stack 28 constant. However, preferably, instead of using a separate microprocessor 22, a microprocessor may be built into temperature controller 32, and such a temperature controller is a conventional item sold, for example, by Omega Corp. of Stamford, Conn.

The temperature of measurement stack 28 is set to a desired temperature by the user through keyboard 24 connected with microprocessor 22.

By controlling the temperature of measurement stack 28 to atmospheric temperature, the same conditions are set as those in a conventional industrial operation using the same chemical sample.

As noted above, the EPA has determined that water vapor is not a contaminant, that is, steam is not considered to be part of the visual emissions as defined by the EPA. Accordingly, in many situations, the effects of water vapor on the smoke detector should be eliminated, since this could affect the output. Thus, in the situation where sample 17 contains water, measurement stack 28 can be held at a temperature above 100° C. so that there will be no contribution by water vapor to the measured smoke. In this regard, the water vapor is made totally gaseous so as not to affect any measurements. Thus, there is no need to provide any complex measurements relating to the water vapor, since there is no water vapor to be taken into account.

Of course, in those situations where water vapor will not affect the final output, or in which there is no or negligible water in the sample, measurement stack 28 can be maintained at a temperature below, for example, 50° C. so as to include water vapor in the measurements.

Two diametrically opposite windows 34 and 36 are provided in measurement stack 28, preferably at a lower position thereof, that is, immediately above upper surface 16 of sample heating block 14. Windows 34 and 36 extend along a line transverse to the longitudinal axis of measurement stack 28.

A laser source 38 is provided on one side of measurement stack 28 in alignment with windows 34 and 36, and a photodetector 40 is provided on the other side of measurement stack 28 in alignment with windows 34 and 36 and with laser source 38. Laser source 38 aims a laser beam 42 through window 34 of measurement stack 28, and laser beam 42 travels through stack 28, exiting through window 36 and impinging at the opposite side on photodetector 40. The amount of light received by photodetector 40 will depend upon the amount of particulate contaminants in the smoke, that is, on the amount of refraction and reflection from the smoke generated by sample 17. In other words, the amount of smoke in the tube is directly proportional to the amount of laser light that is refracted.

Laser source 38 is used to ensure a collimated beam at a constant light intensity. Preferably, a helium neon laser used to provide maximum opacity readings as defined by the EPA, since maximum opacity readings are found with red light. In like manner, photodetector 40 is preferably optimized for red light, so as to be extremely sensitive to changes in light intensity from laser source 38.

Photodetector 40 is connected to a photodetector meter 44 by means of a coaxial cable 46 in order to maintain signal integrity. Specifically, photodetector meter 44 measures light output in milliwatts and produces a standardized output signal in the range of −1 to 1 volt.

The output of photodetector meter 44 is connected by a coaxial cable 48 to a data acquisition board 50 which is designed to minimize noise in the data. Data acquisition board 50 is a high performance signal processor which samples data at a rate of, for example, 100 times per second. Data acquisition board 50 preferably plugs into any open expansion slot on an IBM Compatible computer or the like which preferably forms microprocessor 22.

Basically, the software that runs data acquisition board 50 generally requires a 386 or better IBM PC Compatible machine. Data from acquisition board 50 is date and time stamped and logged to a data file for archiving.

Thus, samplings are taken from the output of photodetector meter 44 at a rate, for example, of 100 times per second for 30 seconds. These sample readings are integrated over time by microprocessor 22 to arrive at a single value corresponding to the amount of generated smoke. Specifically, microprocessor 22 then compares these values with a standard value set, for example, by the EPA for emission, and which is stored in memory (not shown) in microprocessor 22. Then, the differences between the sample values and the standard are integrated over a period of time to provide a normalized number which represents the amount of smoke evolved from the sample chemical. Since the purpose of this equipment is to provide documentation on the amount of smoke generated from various samples, this number which is generated by integrating the difference between the sample and the standard is directly comparable between two different samples, allowing for instant determination of which sample produces more or less smoke. By using a single number which is the integral of the reduction in the transmission of visible light relative to the standard, smoke opacity detector 10 generates results that are comparable despite varying rates of smoke evolution from different chemicals. The results can be viewed on a monitor 52, and of course, a hard copy can be printed out by a printer (not shown) if desired.

Thus, if the integrated value is greater than the standard or set value, emission is too high and another chemical must be chosen. In this regard, a manufacturer can test chemicals under the same conditions as normally met during manufacturing, without actually using the chemical in an actual industrial operation, such as a textile operation.

The following is a typical sample run utilizing smoke opacity detector 10, in which sample 17 is volatilized at a temperature of 350° F. (177° C.).

Step 1: A representative chemical sample is obtained from an industrial plant. Step 2: Smoke opacity detector 10 is turned on, and temperature controller 20 for sample heating block 14 is set at 177° C. Further, since sample 17 contains water, temperature controller 32 for measurement stack 28 is set at 102° C. Step 3: While temperature controllers 20 and 32 are equilibrating, computer or microprocessor 22 is turned on so as to load the smoke opacity software program. Step 4: Meter 44 confirms the operation of laser source 38 and photodetector 40. Step 5: Once temperature controllers 20 and 32 confirm that the set temperatures have been reached, 1 milliliter of sample 17 is withdrawn from a sample container (not shown) into a precision pipette (not shown). Step 6: The data collecting operation of the smoke opacity software by microprocessor 22 is initiated. Step 7: When prompted by the program, the 1 milliliter sample 17 is introduced through sample injection port 26. Step 8: Sample 17 lands on upper surface 16 of sample heating block 14, so that smoke is generated therefrom. Step 9: While the program is running, the operator sees a real time graphical display of the smoke opacity of sample 17 on monitor 52, along with a real time graphical display of the difference between the smoke opacity of sample 17 and the smoke opacity of a standard which has previously been run.

Step 10: At the completion of data acquisition, the smoke opacity program returns to the main menu.

Step 11: The operator then chooses the Analyze Option.

Step 12: Data from the run is loaded into a spreadsheet program. The data is analyzed and the integral of the difference between sample 17 and the standard is calculated. This integral is the value which represents the smoking potential of sample 17.

Step 13: If a new sample needs to be tested, temperature controllers 20 and 32 would be set to the new temperatures, and steps 5 through 12 repeated.

Step 14: If the operator desires to compare the smoking potential of sample 17 with that of a previously run sample, the operator would compare the integral of sample 17 with the integral of the previously run sample. In such case, if the integral of sample 17 is larger than that of the previously run sample, then sample 17 produces more smoke than does the previously run sample.

The results for two samples XXX (sample 17) and WWW (previously run sample) are shown below as follows, where the temperature of sample heating block 14 for both samples was 176° C., the temperature of measurement stack 28 for both samples was 102° C., the sample size for both samples was 1 milliliter and both were compared against toluene:

| Sample ID | Data | Integral Data |
| --- | --- | --- |
| XXX | 1/10/93 | 1120 |
| WWW | 1/1/93 | 851 |

Based upon these results, it can be seen that sample WWW produces 24%=(100%−851/1120) less smoke than sample XXX at a sample temperature of 176° C.

Thus, smoke opacity detector 10 permits a company to determine how much smoke is evolved from any given chemical in its facility. By careful screening of the chemicals that are used, the company can reduce visual emissions from the facility while minimizing the use of expensive air pollution control techniques. Further, a company that is not in compliance with federal, state, or local environmental enforcement agencies can use smoke opacity detector 10 to identify what chemicals are causing the emissions problems and take quick effective action to avoid legal problems.

The present invention uses the following software program as a shell that permits operation of microprocessor 22:

```
10 REM program prints menu and allows selection of setup and
   analysis
15 C=O
20 CLS
25 PRINT:PRINT:PRINT"*******************************************
   **********
30 PRINT" Welcome to the Clean Smoke Test System - Choose
   option below":
34 PRINT"******************************************************
35 PRINT:PRINT:PRINT"                                    ! CAUTION !
36 PRINT" POWER METER RANGE MUST BE THE SAME FOR BOTH
```

-continued

```
      CALIBRATION
 37   PRINT"                              ! AND DATA RUNS !":PRINT:PRINT
 38   PRINT " 0 . to quit program but stay in basic [eliminate
      choice when done]":PRINT
 40   PRINT" 1 . Perform a calibration run
 50   PRINT" 2 . Perform a data run
 60   PRINT" 3 . Analyze data
 61   PRINT" 4 . Quit Program and return to DOS":PRINT
 62   PRINT" 5 . Enter Labtech Notebook for System Maintenance
 65   PRINT:PRINT:PRINT:PRINT:
 70   INPUT " Enter choice now";C
 75   IF C=4 THEN CLS:SYSTEM
 77   IF C=O THEN CLS:LIST:STOP
 80   IF C=1 THEN SHELL "copy setup   st_stnd" :GOTO 120
Ok
Ok
list 81-400
 90   IF C=2 THEN SHELL "copy setup   comp":GOTO 220
100   IF C=3 THEN SHELL "c:  123   123":GOTO 330
105   IF C=5 THEN SHELL "nb":GOTO 330
110   GOTO 10
120   SHELL "go":GOTO 330
220   SHELL "go"
330   GOTO 10
Ok
```

The following program for microprocessor 22 deals with the data acquisition, which obtains the values from the samplings, determines the difference between the samplings and the standard value and integrates the same. This program includes a screen setup sub-program for viewing the same on monitor 52, a trace setup sub-program for producing graphical results, a normal data acquisition/control setup sub-program for performing the aforementioned calculations and determinations and a files setup sub-program for storing the same in various files.

| Current Value: 1 | SCREEN SETUP | |
|---|---|---|
| Number of Windows [0 . . . 15] | 1 | |
| Window Number | 1 | |
| Left Limit, x0 [0.0 . . . 1.0] | 0.150 | |
| Lower Limit, y0 [0.0 . . . 1.0] | 0.106 | |
| Right Limit, x1 [0.0 . . . 1.0] | 0.990 | |
| Upper Limit, y1 [0.0 . . . 1.0] | 0.990 | |
| Y Axis Title | Signal, | |
| X Axis Title | Time, se | |
| Length of Time (X) Axis in sec. | 30.000 | |
| Format of Time Axis | [NNNN] | |
| Minimum X Tic Value | 0.000 | |
| Maximum X Tic Value | 30.000 | |
| Number of X tics (0 . . . 11) | 11 | |
| Minimum Y Tic Value | −10.000 | |
| Maximum Y Tic Value | 60.000 | |
| Number of Y tics [0 . . . 11] | 10 | |
| Window Color | [Green] | |
| Scroll Size [5.0E-02 . . . 1.0] | 0.500 | |

Abbreviations - TD: Time of Day, ET: Elapsed Time, H: Hours, M: Min., S: sec.

| Current Value: 2 | TRACE SETUP | |
|---|---|---|
| Number of Traces [0 . . . 50] | 2 | |
| Trace Number | 1 | 2 |
| Window Number [1 . . . 15] | 1 | 1 |
| Trace Color | [Black] | [Red] |
| Line Type | [Solid] | [Solid] |
| Data Point Symbol | [None] | [None] |
| Y Block Number | 1 | 4 |
| Y Minimum Displayed Value | −10.000 | −1.000 |
| Y Maximum Displayed Value | 30.000 | 20.000 |
| Trace Type | [T vs Y] | [T vs Y] |
| For Meters only: | | |
| No. of Decimal Places | 3 | 2 |
| For Type XY Only: | | |
| X Block Number | 1 | 1 |
| X Minimum Displayed Value | 0.000 | 0.000 |

-continued

| | | |
|---|---|---|
| X Maximum Displayed Value | 10.000 | 10.000 |

| Current Value: 4 | NORMAL DATA ACQUISITION/ CONTROL SETUP |
|---|---|
| Number of Blocks [0 . . . 250] | 4 |
| Current Block(s) [n or n . . . m] | 1 |
| Block Type | [Analog Input] |
| Block Name | |
| Block Unit | Volts |
| Interface Device | [1: PCL-812/780] |
| Interface Pt./Channel No. [0 . . . 15] | 1 |
| Input Range | [±2 V] |
| Scale Factor | 10.000 |
| Offset Constant | 0.000 |
| Buffer Size | 500 |
| Number of Iterations [1 . . . 2000000000] | 1 |
| Number of Stages [1 . . . 4] | 1 |
| Stage Number | 1 |
| Sampling Rate, Hz [1E-30 . . . 1E3] | 30.000 |
| Stage Duration, sec. [0 . . . 1E8] | 30.000 |
| Start/Stop Method | [Immed.] |
| Trigger Block | 1 |
| Trigger Pattern to AND [0 . . . 255] | 0 |
| Trigger Pattern to XOR [0 . . . 255] | 0 |
| | MORE |

| Current Value: 1 | FILES SETUP | |
|---|---|---|
| Number of Files [0 . . . 12] | 1 | |
| Current File [1 . . . 1] | 1 | |
| Data File Name | data&.prn | |
| Data Storage Mode | [ASCII Real] | |
| Number of Header Lines [0 . . . 4] | 4 | |
| Header Line 1 | Clean Smoke Testing Program | |
| Header Line 2 | Data Correlation Report | |
| Header Line 3 | File Run at $TIME | |
| Header Line 4 | File Run on $DATE | |
| Data File Opening mode | [Delete Existing File] | |
| Data File Closing Mode | [End of Run] | |
| Number of Records to Close File | 0 | |
| Number of Hours to Close File | 0.000 | |
| No. of Columns in File [1 . . . 100] | 2 | |
| File Column Number | 1 | 2 |
| Block Number | 2 | 4 |
| Block Name | time | data |
| Block Units | | |
| Field Width [ASCII Files] | 12 | 12 |
| Decimal Places [ASCII Real Files] | 4 | 4 |

In file name, '&' includes a sequence no., and '@' includes the date.

In addition to detecting the smoke opacity of sample 17, testing of smoke by infrared (IR) spectrophotometry can also be accomplished. In this regard, as shown in FIG. 1, two diametrically opposite windows 54 and 56 are provided in measurement stack 28, preferably at position above windows 34 and 36. Windows 54 and 56 extend along a line transverse to the longitudinal axis of measurement stack 28.

An IR light source 58 is provided on one side of measurement stack 28 in alignment with windows 54 and 56, and a photodetector 60, which is adapted to detect only IR light, is provided on the other side of measurement stack 28 in alignment with windows 54 and 56 and with IR light source 58. IR light source 58 aims an IR beam 62 through window 54 of measurement stack 28, and IR beam 62 travels through stack 28, exiting through window 56 and impinging at the opposite side on photodetector 60. In response thereto, photodetector 60 transmits a signal along coaxial cable 64 to microprocessor 22 for analysis of the spectra in order to determine the molecular structure of the material.

Further, a GC port 66 for retrieving smoke for gas chromatography analysis is provided at window 56, and a valve 68 is provided to close or open GC port 66. When GC port 66 is closed, smoke travels through the entire length of stack 28. However, because GC port 66 is maintained at a lower pressure than the upper end of stack 28, when valve 68 is open, the smoke will seek the point of lower pressure, that is, greater pressure differential, and travel to GC port 66. GC port 66 supplies the smoke to a gas chromatograph 70 for analysis, for example, to measure the molecular composition of the smoke.

In addition, an inlet reference stream conduit 72 is provided at the lower end of stack 28 in order to supply a reference gas stream to stack 28. For example, the reference gas stream may contain smoke which is used to calibrate the instrumentation. Alternatively, an inert gas may be supplied through conduit 72 to flush the smoke into GC port 66.

Although the invention has been discussed relative to a textile finishing operation, it is not so limited, and has much wider applicability.

Having described specific preferred embodiments of the invention with reference to the accompanying drawings, it will be appreciated that the present invention is not limited to those precise embodiments and that various changes and modifications can be effected therein by one of ordinary skill in the art without departing from the scope or spirit of the invention as defined by the appended claims.

What is claimed is:

1. A smoke opacity detector comprising:
   a sample chamber;
   sample heating block means in said sample chamber for heating a sample;
   first temperature control means for controlling the temperature of said sample heating block means to a desired temperature;
   measurement stack means positioned above said sample heating block means for receiving smoke resulting from heating of said sample by said sample heating block means;
   light means for projecting a light beam through said smoke in said measurement stack means;
   photodetector means for detecting the amount of light from said light means that passes through said smoke in said measurement stack means;
   determining means for determining the amount of smoke resulting from heating of the sample, in response to the light detected by said photodetector means; and
   means for selectively eliminating conditions of water vapor in the determination of the amount of smoke by said determining means, said means for selectively eliminating including heating means for heating said measurement stack means and second temperature control means for selectively controlling the temperature of said measurement stack means to a selected temperature:
   above 100° C. to render said water vapor gaseous and thereby eliminate affects of water vapor on said determination, and
   a temperature below 100° C. to include affects of water vapor on said determination.

2. A smoke opacity detector according to claim 1, wherein said sample heating block means includes heating wire means therein for heating said sample heating block means.

3. A smoke opacity detector according to claim 1, wherein said heating block means is heated to a temperature in the range of approximately 50° C. to 600° C.

4. A smoke opacity detector according to claim 1, wherein said measurement stack means is of a generally tubular nature and is positioned directly above said sample heating block means.

5. A smoke opacity detector according to claim 1, wherein said measurement stack means extends along a longitudinal axis thereof and includes first and second diametrically opposite windows therein which extend along a line transverse to said longitudinal axis.

6. A smoke opacity detector according to claim 5, wherein said light means is positioned adjacent said first window so as to project said light beam through said first window toward said second window, and said photodetector means is positioned adjacent said second window for detecting the amount of light from said light means that passes through said first window, said smoke in said measurement stack means and said second window.

7. A smoke opacity detector according to claim 6,
   wherein said measurement stack includes third and fourth diametrically opposite windows therein which extend along a line transverse to said longitudinal axis, and which are positioned at heights above said first and second windows; and
   further including:
   infrared light means positioned adjacent said third window so as to project an infrared light beam through said third window toward said fourth window, and
   infrared photodetector means positioned adjacent said fourth window for detecting the amount of infrared light from said infrared light means that passes through said third window, said smoke in said measurement stack means and said fourth window, and for supplying an output signal to a microprocessor for infrared spectrophotometry.

8. A smoke opacity detector according to claim 6,
   wherein said measurement stack includes an opening positioned at a height above said first and second windows; and
   further including GC port means for retrieving smoke for gas chromatography analysis from said opening.

9. A smoke opacity detector according to claim 8, further including conduit means for supplying a gas to a lower end of said stack means.

10. A smoke opacity detector according to claim 1, wherein said light means includes a laser light source.

11. A smoke opacity detector according to claim 10, wherein said laser light source is a red helium neon laser light source.

12. A smoke opacity detector according to claim 1, wherein said determining means includes means for determining a difference between a determined value corresponding to the amount of smoke resulting from heating of the sample and a standard value, and for integrating said difference to produce an output which is a determination of whether the determined value is greater or less than said standard value.

13. A smoke opacity detector according to claim 1, wherein said determining means includes a microprocessor.

14. A smoke opacity detector according to claim 1, wherein said heating means of said means for selectively eliminating includes wire means in said measurement stack means for heating said measurement stack means to selectively render said water vapor gaseous to thereby eliminate affects of water vapor on said determination.

15. A smoke opacity detector according to claim 1, further including sample injection port means extending through said chamber for supplying a predetermined amount of said sample through said measurement stack means onto said sample heating block means.

16. A method of detecting smoke opacity, comprising the steps of:
heating a sample on a sample heating block means in a chamber to produce smoke;
controlling the temperature of said sample heating block means to a desired temperature;
projecting a light beam through said smoke passing through a measurement stack means positioned above said sample heating block means;
detecting the amount of light from said light means that passes through said smoke in said measurement stack means;
determining the amount of smoke resulting from heating of the sample, in response to the amount of detected light; and
selectively eliminating conditions of water vapor in the determination of the amount of smoke, said step of selectively eliminating including the steps of heating said measurement stack means and selectively controlling the temperature of said measurement stack means to a selected temperature:
above 100° C. to render said water vapor gaseous and thereby eliminate affects of water vapor on said determination, and
a temperature below 100° C. to include affects of water vapor on said determination.

17. A method according to claim 16, wherein said sample is heated to a temperature in the range of approximately 50° C. to 600° C. in said step of heating.

18. A method according to claim 16, wherein said measurement stack means is of a generally tubular nature and is positioned directly above said sample heating block means.

19. A method according to claim 18, wherein:
said measurement stack means extends along a longitudinal axis thereof and includes first and second diametrically opposite windows therein which extend along a line transverse to said longitudinal axis,
said light beam is passed through said first window, said smoke in said measurement stack means and said second window, and
the amount of light from said light means that passes through said smoke in said measurement stack means and said second window is detected by a photodetector means.

20. A method according to claim 16, wherein said light beam is a laser light beam.

21. A method according to claim 20, wherein said laser light beam is a red helium neon laser light beam.

22. A method according to claim 16, wherein said step of determining includes the steps of:
determining a difference between a determined value corresponding to the amount of smoke resulting from heating of the sample and a standard value, and
integrating said difference to produce an output which is a determination of whether the determined value is greater or less than said standard value.

23. A method according to claim 16, further including the step of supplying a predetermined amount of said sample through said measurement stack means onto said sample heating block means.

24. A method according to claim 16, further including the step of performing infrared spectrophotometry by passing an infrared light beam through the smoke in said stack means.

25. A method according to claim 16, further including the step of performing gas chromatography analysis by retrieving smoke through a GC port in communication with an opening of said stack means.

26. A method according to claim 16, further including the step of supplying a gas to a lower end of said stack means.

* * * * *